(12) United States Patent
Belov et al.

(10) Patent No.: US 7,964,097 B2
(45) Date of Patent: Jun. 21, 2011

(54) MULTICAPILLARY COLUMN FOR CHROMATOGRAPHY AND SAMPLE PREPARATION

(76) Inventors: Yuri P. Belov, State College, PA (US); Carlo G. Pantano, Pennsylvania Furnace, PA (US); Subramania Ramachandran, State College, PA (US); Vladimir N. Sidelnikov, Novosibirsk (RU)

( * ) Notice: Subject to any disclaimer, the term of this patent is extended or adjusted under 35 U.S.C. 154(b) by 1092 days.

(21) Appl. No.: 11/633,713

(22) Filed: Dec. 5, 2006

(65) Prior Publication Data
US 2007/0075007 A1    Apr. 5, 2007

Related U.S. Application Data

(62) Division of application No. 10/955,377, filed on Sep. 30, 2004, now Pat. No. 7,166,212.

(60) Provisional application No. 60/507,474, filed on Sep. 30, 2003.

(51) Int. Cl.
   *B01D 15/08*    (2006.01)
(52) U.S. Cl. ............ 210/198.2; 210/635; 210/656; 210/500.23; 210/502.1; 96/101
(58) Field of Classification Search ........ 210/635, 210/656, 198.2, 500.23, 502.1; 96/101
   See application file for complete search history.

(56) References Cited

U.S. PATENT DOCUMENTS

| | | |
|---|---|---|
| 3,570,673 A | 3/1971 | Dutz et al. |
| 4,043,905 A | 8/1977 | Novotny et al. |
| 4,045,352 A | 8/1977 | Rembaum et al. |
| 4,214,020 A | 7/1980 | Ward et al. |
| 4,293,413 A | 10/1981 | Schnell |
| 4,293,415 A | 10/1981 | Bente, III et al. |
| 4,424,127 A | 1/1984 | Roeraade |
| 4,654,265 A | 3/1987 | Kamei et al. |
| 4,657,742 A | 4/1987 | Beaver |
| 4,689,267 A | 8/1987 | Takamizawa et al. |
| 4,715,105 A | 12/1987 | Beaver |
| 4,818,264 A | 4/1989 | Langhorst |
| 4,957,620 A | 9/1990 | Cussler |
| 4,999,164 A | 3/1991 | Puchinger et al. |
| 5,092,155 A | 3/1992 | Rounbehler et al. |
| 5,092,219 A | 3/1992 | Rounbehler et al. |
| 5,154,822 A | 10/1992 | Simpson |
| 5,160,627 A | 11/1992 | Cussler et al. |
| 5,194,333 A | 3/1993 | Ohnaka et al. |
| 5,395,521 A | 3/1995 | Jagadeeswaran |
| 5,438,127 A | 8/1995 | Woodard et al. |
| 5,460,781 A | 10/1995 | Hori et al. |
| 5,552,047 A | 9/1996 | Oshida et al. |

(Continued)

FOREIGN PATENT DOCUMENTS

CH    654666    2/1986

(Continued)

OTHER PUBLICATIONS

Pereiro, Isaac R., et al., Characterization of multicapillary gas chromatography . . . , Journal of Chromatography A, Feb. 6, 1998, pp. 359-370, vol. 795, Issue 2.

(Continued)

*Primary Examiner* — Ernest G Therkorn
(74) *Attorney, Agent, or Firm* — Grant Anderson LLP (57) ABSTRACT

A multicapillary column especially useful for liquid chromatography and sample preparation comprising a plurality of uniform capillaries coated with an insoluble stationary phase, wherein the thickness of the stationary phase is correlated with the radius of the individual capillaries for high efficiency.

10 Claims, 10 Drawing Sheets

U.S. PATENT DOCUMENTS

| | | | |
|---|---|---|---|
| 5,578,204 A | 11/1996 | Bartholmes et al. |
| 5,610,290 A | 3/1997 | Woodard et al. |
| 5,616,701 A | 4/1997 | Woodard et al. |
| 5,774,779 A | 6/1998 | Tuchinskiy |
| 5,851,491 A | 12/1998 | Moulton |
| 5,876,918 A | 3/1999 | Wainwright et al. |
| 6,007,609 A | 12/1999 | Semerdjian et al. |
| 6,045,757 A | 4/2000 | Moriarty et al. |
| 6,048,457 A | 4/2000 | Kopaciewicz et al. |
| 6,117,394 A | 9/2000 | Smith |
| 6,143,252 A | 11/2000 | Haxo, Jr. et al. |
| 6,162,341 A | 12/2000 | Nordman et al. |
| 6,168,948 B1 | 1/2001 | Anderson et al. |
| 6,174,352 B1 | 1/2001 | Semerdjian et al. |
| 6,174,673 B1 | 1/2001 | Short et al. |
| 6,231,739 B1 | 5/2001 | Nordman et al. |
| 6,270,674 B1 | 8/2001 | Baurmeister et al. |
| 6,306,659 B1 | 10/2001 | Parce et al. |
| 6,309,828 B1 | 10/2001 | Schleifer et al. |
| 6,325,114 B1 | 12/2001 | Bevirt et al. |
| 6,329,209 B1 | 12/2001 | Wagner et al. |
| 6,333,088 B1 | 12/2001 | Le Febre et al. |
| 6,338,802 B1 | 1/2002 | Bodner et al. |
| 6,357,484 B1 | 3/2002 | Semerdjian et al. |
| 6,387,236 B2 | 5/2002 | Nordman et al. |
| 6,387,331 B1 | 5/2002 | Hunter |
| 6,406,921 B1 | 6/2002 | Wagner et al. |
| 6,416,716 B1 | 7/2002 | Shukla et al. |
| 6,482,362 B1 | 11/2002 | Smith |
| 6,537,502 B1 | 3/2003 | Shukla et al. |
| 6,576,478 B1 | 6/2003 | Wagner et al. |
| 6,582,969 B1 | 6/2003 | Wagner et al. |
| 6,596,237 B1 | 7/2003 | Borrelli et al. |
| 6,596,545 B1 | 7/2003 | Wagner et al. |
| 6,635,201 B1 | 10/2003 | Kopaciewicz et al. |
| 6,638,482 B1 | 10/2003 | Ackley et al. |
| 6,640,588 B2 | 11/2003 | Semerdjian |
| 6,743,633 B1 | 6/2004 | Hunter |
| 6,759,126 B1 | 7/2004 | Malik et al. |
| 6,780,314 B2 | 8/2004 | Jinno et al. |
| 6,780,582 B1 | 8/2004 | Wagner et al. |
| 6,794,127 B1 | 9/2004 | Lafferty et al. |
| 6,830,717 B2 | 12/2004 | Kopaciewicz et al. |
| 6,866,824 B2 | 3/2005 | Lafferty et al. |
| 6,870,165 B2 | 3/2005 | Amirkhanian et al. |
| 6,875,354 B1 | 4/2005 | Kopaciewicz et al. |
| 6,886,824 B2 | 5/2005 | Johdai et al. |
| 6,972,183 B1 | 12/2005 | Lafferty et al. |
| 6,992,181 B2 | 1/2006 | Tooke et al. |
| 7,118,657 B2 | 10/2006 | Golovchenko et al. |
| 7,118,671 B2 | 10/2006 | Kumakhov et al. |
| 7,122,640 B2 | 10/2006 | Gjerde et al. |
| 7,151,167 B2 | 12/2006 | Gjerde et al. |
| 7,166,212 B2 | 1/2007 | Belov et al. |
| 7,208,072 B2 | 4/2007 | Amirkhanian et al. |
| 7,247,469 B2 | 7/2007 | Wagner et al. |
| 7,271,895 B2 | 9/2007 | Khamizov et al. |
| 7,309,409 B2 | 12/2007 | Amirkhanian et al. |
| 7,595,026 B2 | 9/2009 | Hudson |
| 2002/0110495 A1 | 8/2002 | Hunt et al. |
| 2003/0007897 A1 | 1/2003 | Creasey |
| 2003/0068317 A1 | 4/2003 | Lee et al. |
| 2003/0173284 A1 | 9/2003 | Baker |
| 2004/0038316 A1 | 2/2004 | Kaiser et al. |
| 2004/0171166 A1 | 9/2004 | Hunter |
| 2004/0224425 A1 | 9/2004 | Gjerde et al. |
| 2004/1019153 | 9/2004 | Lubda et al. |
| 2005/0003211 A1 | 1/2005 | Harada et al. |
| 2005/0139536 A1 | 6/2005 | Belov et al. |
| 2005/0178709 A1 | 8/2005 | Nakanishi et al. |
| 2005/0254995 A1 | 11/2005 | Sostek et al. |
| 2005/0281710 A1 | 12/2005 | Crabtree |
| 2006/0093518 A1 | 5/2006 | Shukla et al. |
| 2006/0216206 A1 | 8/2006 | Hudson et al. |
| 2006/0201881 A1 | 9/2006 | Marcus et al. |
| 2007/0017870 A1 | 1/2007 | Belov et al. |
| 2007/0071649 A1 | 3/2007 | Marcus |
| 2007/0075007 A1 | 4/2007 | Belov et al. |
| 2007/0111194 A1 | 5/2007 | Pellaux et al. |
| 2007/0116607 A1 | 5/2007 | Wang et al. |
| 2007/0215543 A1 | 9/2007 | Haidle |

FOREIGN PATENT DOCUMENTS

| | | |
|---|---|---|
| DE | 4443754 | 6/1996 |
| EP | 0729028 | 8/1996 |
| EP | 0926492 | 11/1998 |
| EP | 1477799 | 11/2004 |
| JP | 61-265567 | 11/1986 |
| JP | 11295282 | 10/1999 |
| JP | 2000-515066 | 11/2000 |
| JP | 2003-251122 | 9/2003 |
| JP | 2004-237142 | 8/2004 |
| JP | 3759910 | 3/2006 |
| RU | 2060498 | 5/1996 |
| RU | 2190846 | 10/2002 |
| SU | 2114427 | 6/1988 |
| SU | 1651200 | 5/1991 |
| WO | WO 02/40131 | 5/2002 |
| WO | WO 03/104814 | 12/2003 |
| WO | WO 2005/032688 | 4/2005 |
| WO | WO 2006/093865 | 9/2006 |
| WO | WO 2008/036091 | 3/2008 |
| WO | WO 2009/121032 | 10/2009 |
| WO | WO 2009/121034 | 10/2009 |

OTHER PUBLICATIONS

Sidelnikov, V.N., et al. Polycapillary chromatography. J. Rus. Chem. Soc., 47, 23-34, 2003.

Alltech Multi-Cap Capillary Column, Bulletin #356, Alltech Inc., 1997.

Multicapilarry columns BeeChrom, Product Catalog for GC, ChemSpace, 2002.

International Preliminary Report on Patentability mailed on: Apr. 3, 2006 in International Application No. PCT/US2004/32958 filed on Sep. 30, 2004 and published as: WO 05/032688 on: Apr. 14, 2005.

International Search Report and Written Opinion: Apr. 5, 2007 in International Application No. PCT/US2006/36719 filed on Sep. 30, 2004 and published as: WO 08/036091 on: Mar. 27, 2008.

International Preliminary Report on Patentability mailed on: Mar. 24, 2009 in International Application No. PCT/US2006/36719 filed on Sep. 30, 2004 and published as: WO 08/036091 on: Mar. 27, 2008.

International Search Report and Written Opinion mailed on: Dec. 8, 2004 in International Application No. PCT/US2004/32958 filed on Sep. 30, 2004 and published as: WO 05/032688 on: Apr. 14, 2005.

International Search Report and Written Opinion mailed on: Nov. 17, 2009 in International Application No. PCT/US2009/038688 filed on Mar. 27, 2009 and published as: WO on: Oct. 15, 2009.

International Preliminary Report on Patentability, mailed on: Sep. 28, 2010 in International Application No. PCT/US2009/038686 filed on Mar. 27, 2009 and published as: WO 09/121032 on: Oct. 1, 2009.

International Search Report and Written Opinion, mailed on: Feb. 3, 2010 in International Application No. PCT/US2009/038686 filed on Mar. 27, 2009 and published as: WO 09/121032 on: Oct. 1, 2009.

Li et al., "Factors influencing polybutadiene deposition within porus chromatographic zirconia," Journal of Chromatography A, 1997, pp. 45-52.

Lobinski et al., "Multicapilary column gas chromatography with element-selective detection", Trac, Trends in Analytical Chemistry, vol. 18, No. 7, pp. 449-460, Jul. 1, 1999.

Sidelnikov et al. "Sol-gel multicapilary columns for gas-solid chromatography", Journal of Chromatography, vol. 1101, No. 1-2,pp. 325-318, Jan. 6, 2006.

Supplemental European Search Report mailed on: Mar. 23, 2010 in Application No. EP 06803941.1 filed Sep. 20, 2006.

Zhdnov, "Dependency of the efficiency of the multicapillary column on the liquid phase loading method," J. Chromatogr A., Sep. 2001 928(2), pp. 201-207.

Fig.5A
Mass-spectrum of the Fraction 3.

| No. | Characteristics | SPE Cartridge | Multicapillary Column |
|---|---|---|---|
| 1 | Collection time | 20-40 minutes | Less than 5 minutes |
| 2 | Amount | 1 - 5 ml samples used | Only 100-200ul of samples |
| 3 | Processing the extract | Extract volume 5-20ml. Needs to be evaporated for the analysis | No concentration or evaporation of the extract required |
| 4 | Reconditioning | Cannot be reconditioned | Reconditioned by washing with methanol and water in 2 min. |
| 5 | Reusability | Cannot be reused | Can be reused many times (at least 50-100 times) depending on the sample to be extracted |
| 6 | Silica particles in the sample | Possibility of fine silica particles in the samples | No silica or other particles in the samples |
| 7 | Auto samplers adaptability | Cannot be used in auto samplers | Easily adaptable to auto samplers |
| 8 | Field use | Requires hard to transport and costly equipment/accessories | Requires only syringes |

Table 1.

*Fig.8*

MULTICAPILLARY COLUMN FOR CHROMATOGRAPHY AND SAMPLE PREPARATION

REFERENCE TO RELATED APPLICATIONS

This application is a Divisional of U.S. patent application Ser. No. 10/955,377 filed Sep. 30, 2004, now U.S. Pat. No. 7,166,212, which claims priority to U.S. Provisional Patent Application No. 60/507,474 filed Sep. 30, 2003.

BACKGROUND OF THE INVENTION

1. Field of the Invention

The present invention relates to a multicapillary column especially useful for liquid chromatography and sample preparation. More particularly, the invention relates to a multicapillary column comprising a plurality of uniform capillaries coated with an insoluble stationary phase, wherein the thickness of the stationary phase is correlated with the radius of the individual capillaries.

2. Background Art

Chromatography is the primary technique for separating complicated mixtures of chemical compounds. This is achieved by passing a sample in a mobile phase through a column containing a stationary phase. Chromatography is distinguished into two branches—gas chromatography ("GC") and liquid chromatography ("LC"), depending on the physical state of the mobile phase. Two types of columns may be used in both gas and liquid chromatography—packed and capillary. Packed columns consist of a tube filled with packing material. The stationary phase is applied to the surface of the packing material. In capillary columns, the stationary phase is applied directly onto the inner wall of the capillary. Capillary columns offer substantial advantages over packed columns.

In gas chromatography, the vast majority of analyses are conducted using capillary columns. Capillary columns for gas chromatography are made from single wide capillaries (about 0.5 mm inner diameter) compatible with standard chromatographic equipment. The columns are further differentiated based on the number of capillaries contained therein. Monocapillary columns consist of a single tube, while multicapillary columns comprise many tubes, allowing for a high sample capacity.

The diffusion of molecules in gases is very fast, due to the low viscosity. Compared to gases, liquids are much more viscous. The diffusion of molecules in liquids is 10,000-100,000 times slower than in gases. To provide rapid mass-transfer, the diameter of capillary columns used for liquid chromatography must be very small, usually less than 20 μm. Due to their minuscule sizes and very low sample capacity, capillary columns for liquid chromatography made from single capillaries are not compatible with standard equipment and cannot be used for routine liquid chromatography analyses.

Methods for the preparation of insoluble stationary phases for liquid chromatography are known. Most of these methods are based on chemical bonding of the stationary phases to the surface of chromatographic supports. However, the use of multicapillary columns in liquid chromatographic applications has been constrained because of technical problems. The primary constraint is that the linear flow rate of the mobile phase in wider capillaries is higher than the flow rate in narrower capillaries. If the phase ratio, i.e. the ratio of the radius of the capillary to the stationary phase film thickness, is the same for all capillaries, the sample will move faster in the wider capillaries. As a result, the efficiency of multicapillary columns is always inferior to that of single capillary columns.

Accordingly, there is a need for an efficient multicapillary column having a high sample capacity, for use in liquid chromatography.

SUMMARY OF THE INVENTION

The invention is a highly efficient multicapillary column especially useful for liquid chromatography and sample preparation. The column contains a plurality of uniform capillaries that are coated with an insoluble stationary phase. The thickness of the stationary phase is correlated with the radius of the individual capillaries for high efficiency.

Another embodiment of the invention is a method of making a multicapillary column for use in chromatography and sample preparation. In such method, the multicapillary column is filled with a stationary phase solution. The stationary phase solution is then moved toward the end of the column. Simultaneously therewith, the column is slowly moved in a heated zone or vacuum to facilitate evaporation of the solvent. After deposition, the stationary phase is cross-linked and/or chemically bonded to the walls of the capillaries, rendering the stationary phase insoluble in the mobile phases.

DETAILED DESCRIPTION OF THE INVENTION

The use of multicapillary columns in liquid chromatographic applications has been constrained because of technical problems. The fundamental problem is that the diameter of the capillaries in multicapillary rods is uniform but not identical. As a result, the mobile phase moves faster in wider capillaries than in narrower capillaries. The efficiency of multicapillary columns is therefore inferior to that of single capillary columns. Thus, in order to manufacture high efficiency multicapillary columns, it is critical that an appropriate technique for the deposition of a stationary phase be employed.

The present invention describes a highly efficient multicapillary column that is especially useful for liquid chromatography. The multicapillary column is also useful for applications such as gas chromatography, supercritical chromatography, electrochromatography, capillary electrophoresis, solid phase extraction, head space analysis, sample concentration, and sample desalting.

Figure 1A:
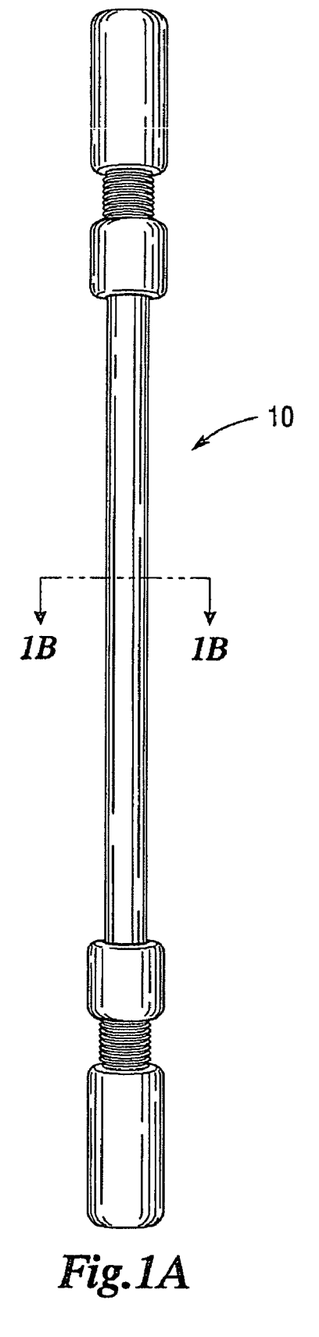
FIG. 1A is a perspective view of a multicapillary chromatography column according to an embodiment of the present invention, the individual capillaries of which are shown in FIG. 1B (cross section)
Figure 1B:
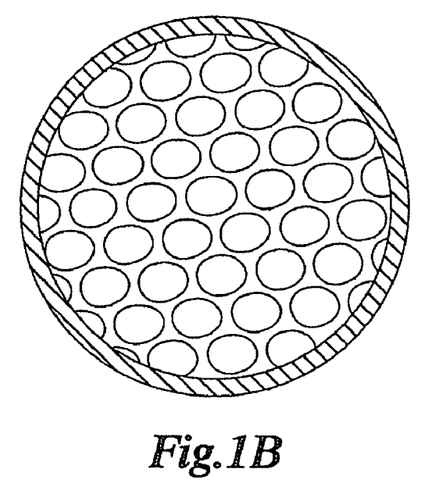

Referring now to FIG. 1, there is shown a cross-section of a multicapillary column 10 according to the present invention. The multicapillary column 10 comprises a rod pierced with a plurality of uniform capillary tubes that receive a sample in a mobile phase at a first end of the column 10 and discharge a separated sample at a second end of the column. The interior of each capillary tube is coated with an insoluble stationary phase, wherein the thickness of the stationary phase is correlated with the radius of the individual capillary tubes. This advantageously ensures that the multicapillary column 10 of the present invention has a substantially higher efficiency than multicapillary columns of the prior art, wherein the thickness of the stationary phase is not correlated with the radius of the capillaries. This improved performance, which derives from the correlation presented herein, makes it possible to employ the multicapillary column 10 as an effective and efficient tool for liquid chromatographic applications.

Figure 2:
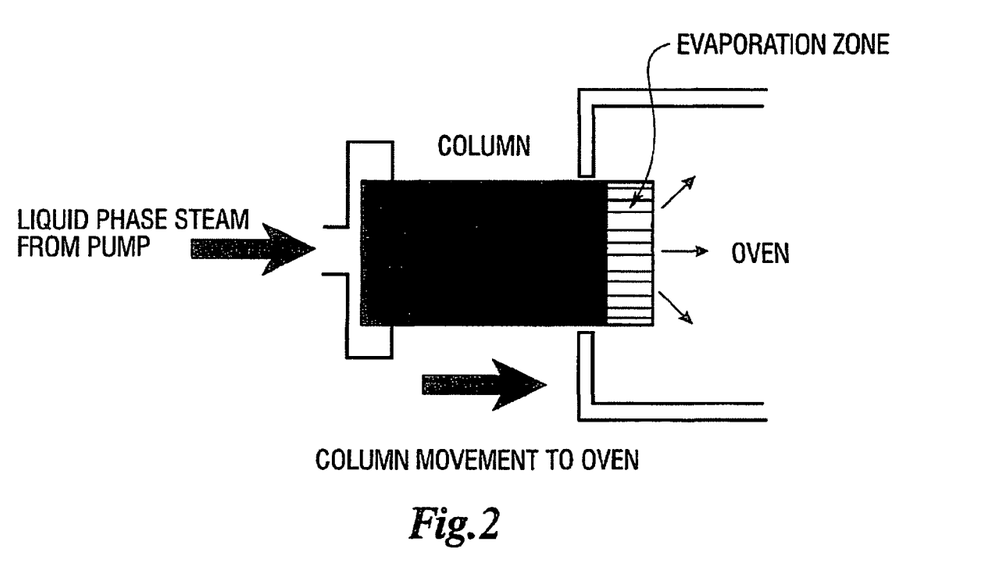
FIG. 2 shows diagrammatically a scheme for deposition of the stationary phase in a multicapillary chromatography column according to an embodiment of the present invention.

In FIG. 2, there is shown a method for preparing the multicapillary column 10 of the present invention. The method comprises introducing a stationary phase solution into a multicapillary column using, for example, pump means. As the stationary phase solution is moved toward the end of the multicapillary column, the column is simultaneously moved in a heated zone (e.g. an oven), vacuum, or other environment that facilitates evaporation of the solvent. Due to the higher velocity of the solution in wider capillaries, the film of the stationary phase that is deposited on the wider capillaries is thicker than the film that is deposited on the more narrow capillaries. After deposition, the stationary phase is cross-linked and/or chemically bonded to the interior walls of the capillaries. The process of the present invention renders the stationary phase material insoluble in the mobile phase (e.g. organic and water-organic solvents).

By varying the thickness of the stationary phase in the individual capillaries, there is obtained a column 10 having high efficiency in liquid chromatographic applications.

Preferred materials for the fabrication of the tubes and rods employed herein include, for example, glass, fused silica, metal (e.g. stainless steel) and plastic (e.g. PEEK polymer). For liquid chromatographic applications, it is often desirable to employ a large number of capillary tubes (e.g. thousands), however, any number of capillary tubes may be employed in the multicapillary column 10 of the present invention. It will also be understood that the multicapillary column 10 can be used with capillary tubes of varying dimensions. For example, the inner diameter of the capillary tubes may range from about 0.1 µm to about 100 µm. The outer diameter of the column 10 may range from about 0.1 mm to about 1 m, while the length of the column may range from about 0.1 mm to about 2 m.

The important relationship between the stationary phase thickness and capillary radius will now be discussed in further detail:

According to Poiseuille's law, the mobile phase velocity in wider capillaries is faster than its velocity in more narrow capillaries. As a result, a sample is eluted from a multicapillary column in the form of a broad peak. This phenomenon is known as peak broadening.

To solve this problem, that is, to optimize the chromatographic efficiency of multicapillary columns, the inventors have correlated the thickness of the stationary phase with the radius of the individual capillaries. During application of the stationary phase, a greater amount settles on the inner surface of wider capillaries. Conversely, a smaller amount settles on the inner surface of narrower capillaries. As a result, the capillaries achieve quasi-uniformity, and the efficiency of the multicapillary column 10 is substantially increased. The following relationship for high peak efficiency has been derived by the inventors:

$$d_f(r) = c_f r^n \quad \text{(Equation 1)}$$

The stationary phase film thickness $d_f$ is proportional to capillary radius r in power n, where n>1; $c_f$ is a constant.

To achieve the highest peak efficiency, the stationary phase thickness $d_f$ should be proportional to capillary radius r in power 3.

For gas chromatographic applications, the foregoing relationship is used to deposit soluble stationary phases (e.g. polydimethylsiloxane) on the surface of multicapillary columns. However, soluble stationary phases cannot be used in liquid chromatography. These phases would simply be washed away with the stream of a mobile phase. Stationary phases for liquid chromatography must be insoluble in the mobile phase.

The present invention exploits the correlation between the thickness of the stationary phase and the radius of individual capillaries for the preparation of multicapillary columns 10 having insoluble stationary phases appropriate for liquid chromatography. The experimental approach used in a method according to the invention involves three steps:

I. Chemical modification of the capillary walls with organosilicon compounds containing double bonds, such as, for example, vinyldimethylethoxysilane. The reaction scheme is illustrated below:

Surface-OH+EtO—SiMe2-CH=CH2→Surface-O—SiMe2-CH=CH2+EtOH

II. Deposition of a soluble stationary phase containing residual double bonds on the surface of capillaries to correlate film thickness with the capillary radius. A representative example of such stationary phase is polybutadiene. A scheme for the physical deposition of linear polybutadiene is shown below (see FIG. 2):

Surface-O—SiMe2-CH=CH2+Polybutadiene in solution→Surface-O—SiMe2-CH=CH2/Polybutadiene on surface III. Immobilization of the stationary phase by cross-linking and bonding it to the capillary walls. This process is based on reactions between the residual double bonds of the stationary phase and double bonds located on the surface of the capillaries. The reaction is conducted at elevated temperatures in the presence of polymerization initiators. This step can be illustrated as follows:

Surface-O—SiMe2-CH=CH2/Polybutadiene on surface→Surface-O—SiMe2-CH2-CH2-Polybutadiene (cross-linked, bonded, and insoluble)

EXAMPLE 1

Modification of Capillary Surface

A 10% solution of vinyldimethylethoxysilane in toluene is pumped at 50 µL/min for six hours through a clean and dry 1.1 mm outer diameter×100 mm multicapillary glass rod pierced with approximately 4,000 capillaries of 10 µm diameter at 105° C. The column is rinsed with toluene, acetone, and methanol and dried with a nitrogen stream.

EXAMPLE 2

Deposition of Polybutadiene

The multicapillary column, prepared as described in Example 1, is filled with a solution consisting of 100 mg polybutadiene (M.W. 3,400) and 0.5 mg dicumyl peroxide in 100 ml pentane. While pumping the solution at 5 µL/min, the opposite end of the column is placed inside an oven heated to 150° C., and the column is moved at a linear speed of 0.5 mm/min (FIG. 2).

EXAMPLE 3

Immobilization of Polybutadiene

The multicapillary column, prepared as described in Example 2, under slow nitrogen flow, is heated at 200° C. for four hours. Multicapillary columns containing poly(ethylene glycol), linear and cross-linked polystyrene, and cross-linked polydimethylsiloxane are also prepared.

EXAMPLE 4

Octadecyl (C-18) Stationary Phase

The 10% solution of octadecyltriethoxysilane in toluene is pumped at 10 µL/min for six hours through a clean and dry 2.3 mm outer diameter×300 mm multicapillary glass rod pierced with approximately 4,000 capillaries of 20 µm diameter at 105° C. While pumping the solution, the opposite end of the multicapillary column is moved at a linear speed of 0.5 mm/min inside the oven heated to 150° C. The column is rinsed with toluene, acetone, and methanol and dried with a nitrogen stream.

A 10% solution of phenyltrimethoxysilane in toluene is used to prepare the stationary phase with phenyl groups. A 10% solution of 3-aminopropyltrimethoxysilane in toluene is used to prepare the stationary phase with amino groups. A 10% solution of (3-glycidoxypropyl)trimethoxysilane in toluene is used to prepare the stationary phase with glycido groups. A 10% solution of N-trimethoxysilylpropyl-N,N,N trimethylammonium chloride in methanol is used to prepare an anion-exchange stationary phase. A 10% solution of 2-(4-chlorosulfonylphenyl)ethyltrimethoxysilane in toluene is used to prepare a cation-exchange stationary phase.

EXAMPLE 5

Immobilization of Trypsin

A solution containing 1.5% trypsin and 0.4 M dicyclohexylcarbodiimide in 7.5 M urea (pH 4.74 with HCl) is pumped through the multicapillary column functionalized with aminopropyl groups, as described in Example 4, at 50 µL/min for one hour. The multicapillary column is washed with a 7.5 M solution of urea and water.

A similar procedure is used for the immobilization of avidin, pepsin, and ovalbumin.

EXAMPLE 6

Figure 3:
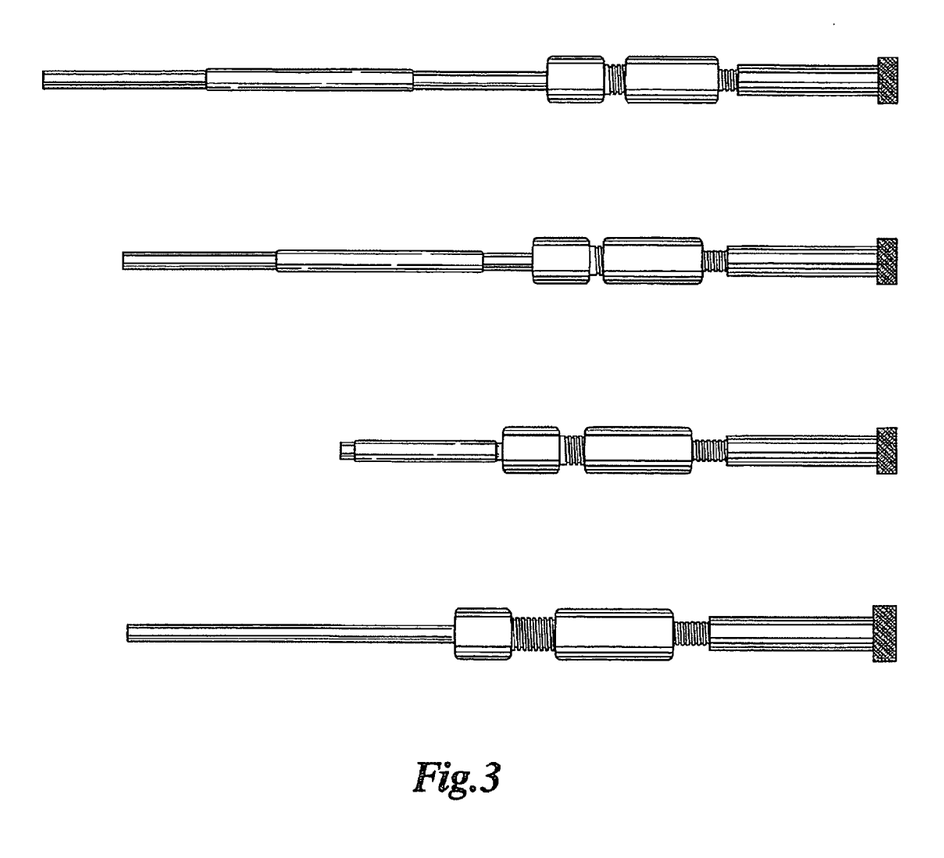
FIG. 3 shows perspective views of different sized multicapillary columns used for HPLC applications and sample preparation.
Figure 4:
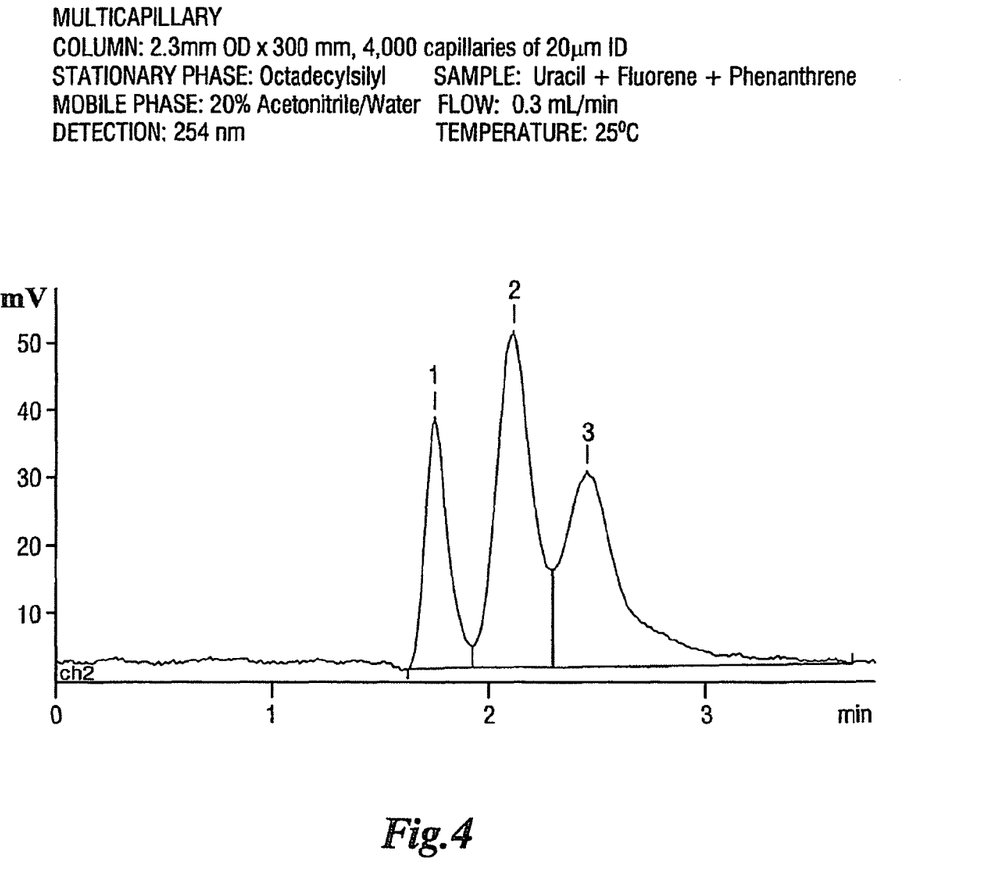
FIG. 4 is a chromatogram showing the separation of a uracil, fluorene, phenanthrene mixture in a multicapillary column according to the present invention.

Liquid Chromatographic Separation of the (Uracil+Fluorene+Phenanthrene) Mixture Referring now to FIG. 4, the (uracil+fluorene+phenanthrene) mixture is separated on the multicapillary column 10 installed in a Shimadzu HPLC instrument using standard HPLC fittings (FIG. 3). The chromatographic conditions and chromatogram are shown reproduced in FIG. 4. The chromatogram shows the uracil peak at about 1.8 minutes, the fluorene peak at about 2.1 minutes, and the phenanthrene peak at about 2.4 minutes.

The example illustrates an HPLC application using the multicapillary column of the present invention, wherein a typical organic mixture can be analyzed in less than three minutes.

EXAMPLE 7

Desalting and Fractionating of Peptides

Figure 5A:
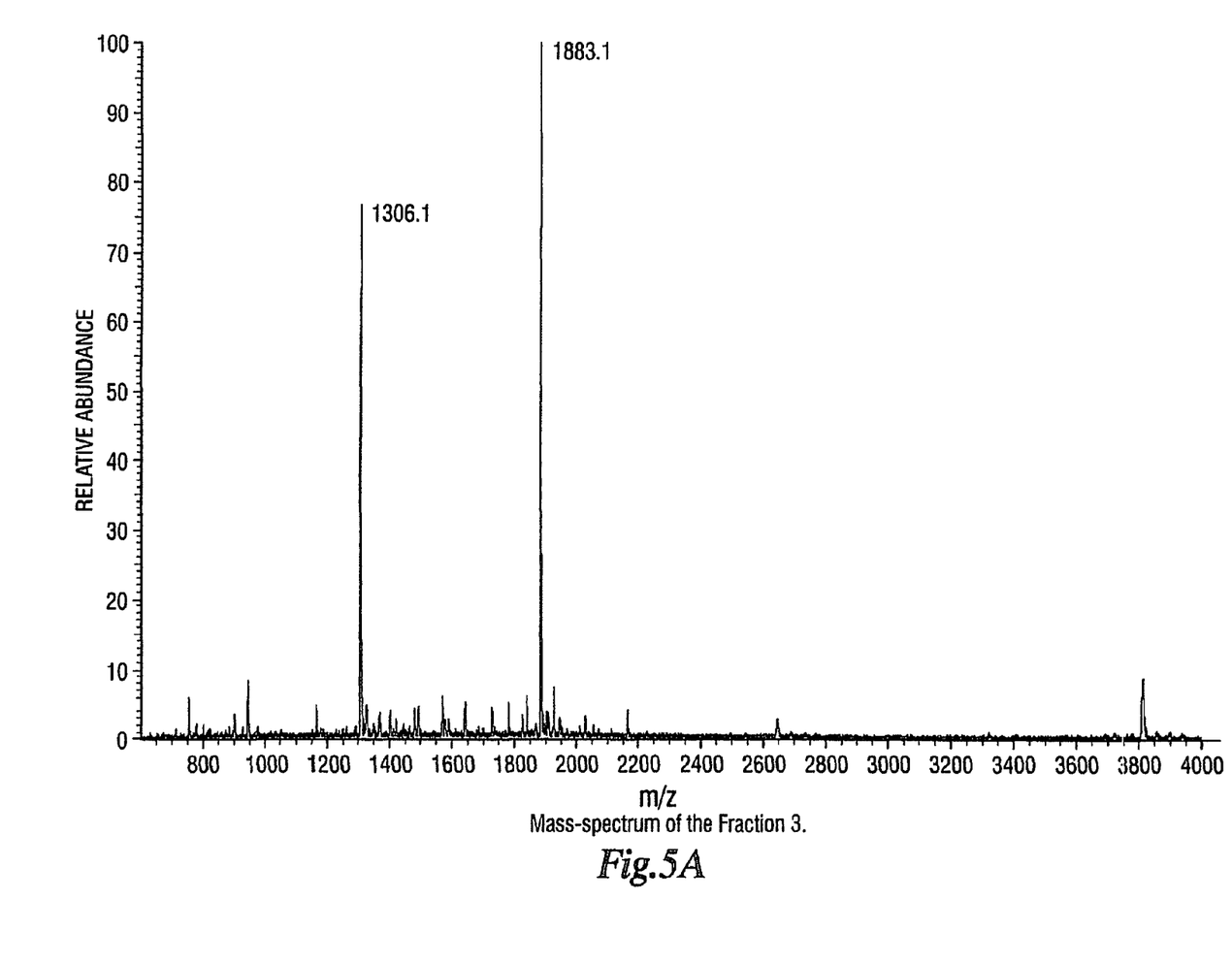
FIGS. 5A and 5B are the mass-spectra demonstrating the performance of a multicapillary column in desalting and fractionating of complex peptide mixtures.
Figure 5B:
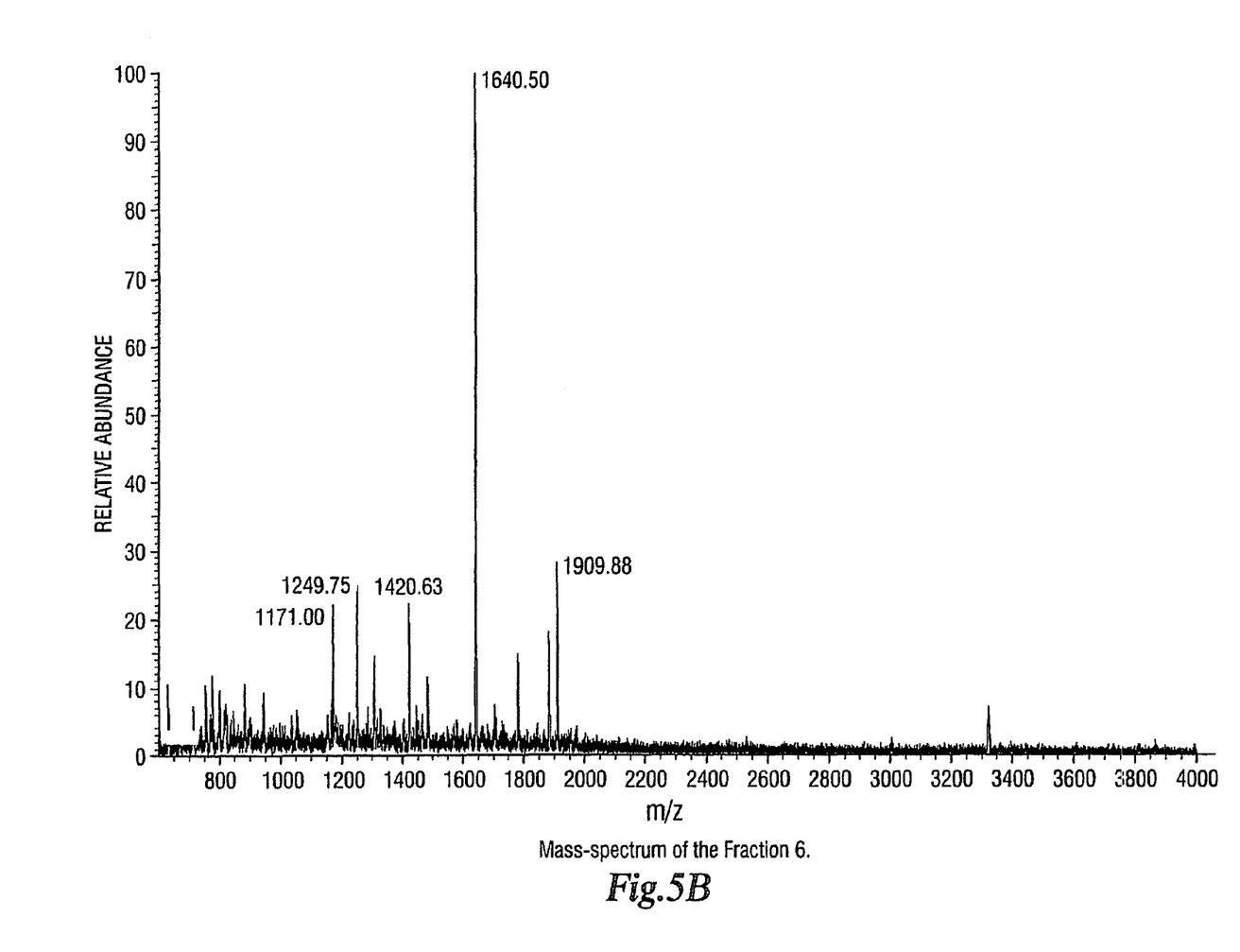

Referring to FIG. 5, a 3 µL volume of the 100 pmole/µL peptide mixture obtained by the enzymatic hydrolysis of bovine serum albumin is introduced in a 10 cm long C-18 column prepared as described in Example 4. The sample is eluted at 100 µL/min at room temperature with 100 µL of deionized water followed by 30 µL of 40% acetonitrile/water. Ten 3 µL 40% acetonitrile/water fractions are collected and analyzed by atmospheric pressure matrix-assisted laser desorption/ionization mass-spectrometry ("MALDI"). Mass-spectra of Fractions 3 and 6 are shown in FIG. 5.

This example illustrates the fractionating ability of the multicapillary column of the present invention, prior to mass-spectrometric analysis of a complex peptide mixture.

EXAMPLE 8

Sample Enrichment for HPLC Analysis

Figure 6A:
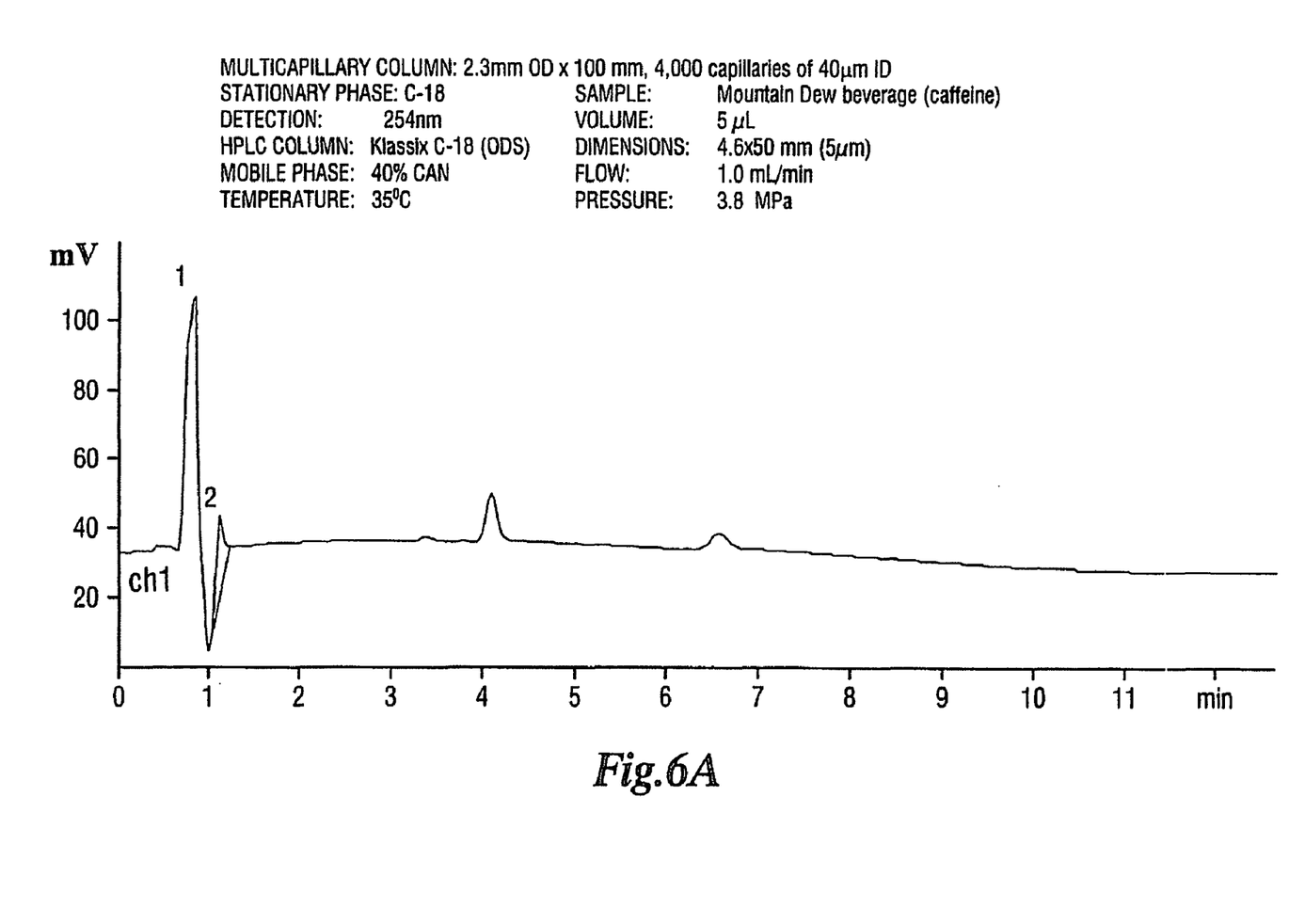
FIG. 6A is a chromatogram showing the performance of a multicapillary chromatography column in sample enrichment.
Figure 6B:
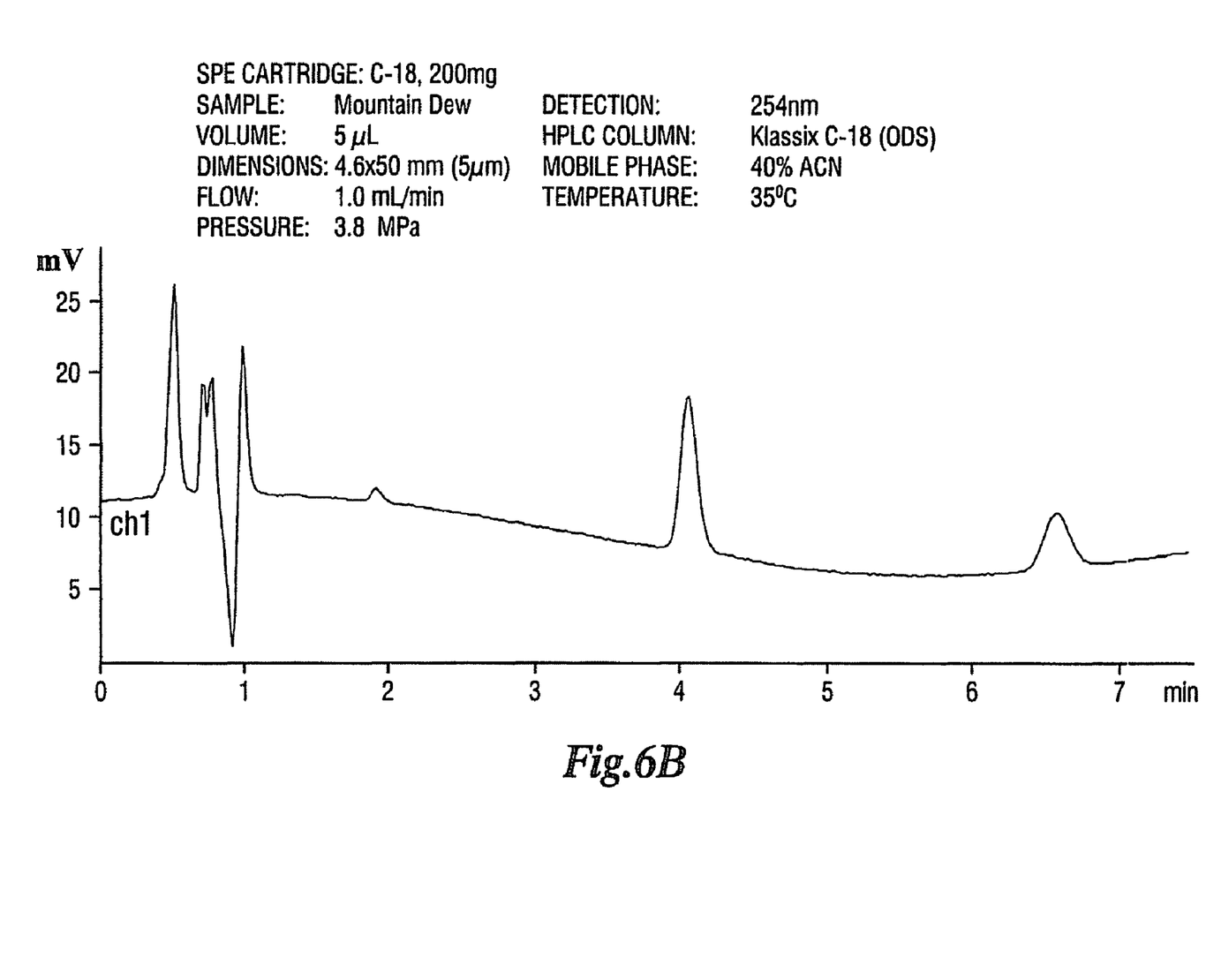
FIG. 6B provides a comparison, showing the performance of an SPE cartridge in sample enrichment.
Figure 8:
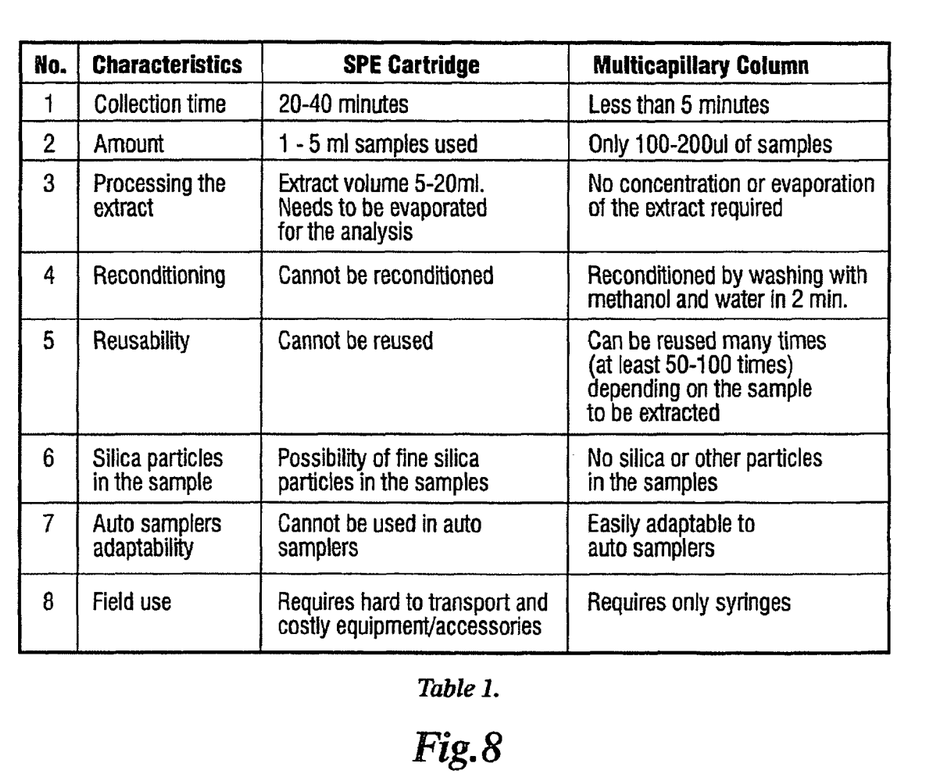
FIG. 8 is a comparative table showing the performance of a conventional solid phase extraction cartridge versus a multicapillary chromatography column according to an embodiment of the present invention.

Referring to FIG. 6, the 2.3 mm outer diameter×100 mm length multicapillary C-18 column containing approximately 1,000 capillaries of 40 µm diameter prepared as described in Example 4 is used for sample enrichment prior to HPLC and GC analyses. Very short HPLC columns known as solid phase extraction ("SPE") cartridges are currently used. Compared to SPE cartridges, multicapillary columns are much faster, simpler and reusable. FIGS. 6A-B and FIG. 8 demonstrate a comparison of the multicapillary column of the present invention versus an SPE cartridge.

The example clearly demonstrates that the multicapillary column of the present invention can effectively replace an SPE cartridge in sample preparation.

EXAMPLE 9

Head Space Enrichment for Gas Chromatographic Analysis

Figure 7:
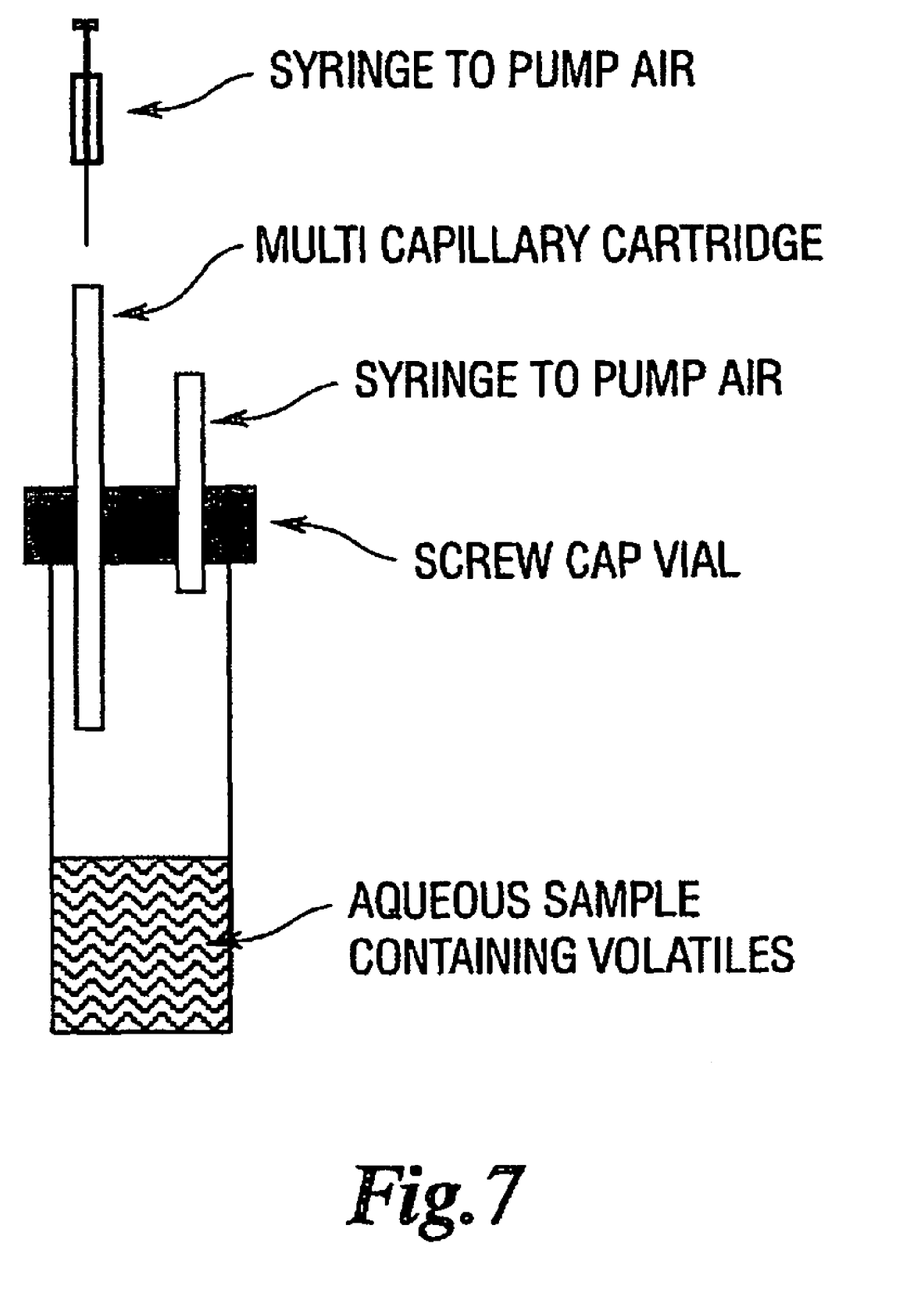
FIG. 7 shows diagrammatically a multicapillary chromatography column for head space analysis of an aqueous sample containing volatiles, according to an embodiment of the present invention.

The 2.3 mm outer diameter×100 mm length multicapillary column containing approximately 4,000 capillaries of 20 µm diameter C-18 column prepared as described in Example 4 for head space sample enrichment prior to gas chromatographic analysis is schematically shown in FIG. 7. A regular 100 μL HPLC syringe is used to push and pull the air through the multicapillary column about five times. Organic volatile compounds above the liquid are adsorbed into the multicapillary column. After this adsorption step, the multicapillary column is removed and eluted with 100 μL of methanol. The methanol extract is analyzed by gas chromatography for the detection of volatile solvents.

This example demonstrates that as compared to conventional methods of head-space analysis, the multicapillary column of the present invention is an easier, faster and simpler alternative.

Examples 1-9 demonstrate the wide scope application of the multicapillary column 10 according to the present invention. Accordingly, it can be seen that the multicapillary column is a highly efficient column that has a high sample capacity and is compatible with existing chromatographic equipment. While the multicapillary column 10 is particularly useful for liquid chromatographic applications (e.g., HPLC analysis), the column can be used in a number of related applications without departing from the scope of the invention. These include, but are not limited to, gas chromatography, supercritical chromatography, electrochromatography, capillary electrophoresis, solid phase extraction, head space analysis, sample concentration, and sample desalting.

Specific examples of the above-mentioned applications include, for example: liquid chromatographic separation of organic compounds, fractionating complicated mixtures prior to instrumental analysis, fractionating peptide mixtures prior to mass-spectrometric analysis, desalting samples prior to instrumental analysis, desalting peptide solutions, desalting protein solutions, sample concentrating prior to instrumental analysis, peptide concentrating prior to mass-spectrometric analysis, and head space concentrating of volatile samples.

While the invention has been particularly shown and described with reference to the examples and preferred embodiments thereof, it will be understood by those skilled in the art that various alterations in form and detail may be made therein without departing from the spirit and scope of the invention.

What is claimed is:

1. A sample preparation multicapillary column, comprising:
    a plurality of capillary tubes having narrower and wider radii arranged in a column; and
    an insoluble stationary phase coated directly on the interior surface of each of the capillary tubes, the stationary phase comprising a thickness correlated with the radius of individual capillary tubes whereby wider capillary tubes include a thickness of the stationary phase greater than the thickness of the stationary phase on narrower capillary tubes, thereby enhancing uniformity of the capillary tubes; and the insoluble stationary phase comprising one or more of a protein, antibody, peptide and glycopeptide.

2. The multicapillary column of claim 1, wherein the capillary tubes comprise a material selected from the group consisting of glass, fused silica, metal, and plastic.

3. The sample preparation device of claim 1, wherein the capillary tubes are formed from fused silica.

4. The sample preparation device of claim 3, wherein the capillary tubes are formed from glass.

5. The sample preparation device of claim 1, wherein an inner diameter of each capillary tube is in the range of about 0.1 .mu.m to about 100 .mu.m.

6. The sample preparation device of claim 5, wherein the inner diameter of each capillary tube is in the range of about 10 .mu.m to about 100 .mu.m.

7. The sample preparation device of claim 5, wherein the inner diameter of each capillary tube is in the range of about 20 .mu.m to about 100 .mu.m.

8. The sample preparation device of claim 1, wherein the thickness of the stationary phase is proportional to the radius of the capillary tube in power n, where n is greater than 1.

9. The sample preparation device of claim 8, wherein the following relationship holds: d.sub.f(r)=c.sub.f r.sup.n where d.sub.f=insoluble stationary phase thickness; c.sub.f=constant; r =capillary radius; and n>1.

10. The sample preparation device of claim 1, wherein the insoluble stationary phase comprises one of the following moieties: protein, antibody, peptide or glycopeptide.

* * * * *